(12) United States Patent
Poehlmann et al.

(10) Patent No.: US 9,315,808 B2
(45) Date of Patent: *Apr. 19, 2016

(54) CELL-SPECIFICALLY EFFECTIVE MOLECULES ON THE BASIS OF SIRNA AND APPLICATION KITS FOR THE PRODUCTION THEREOF AND USE THEREOF

(75) Inventors: Tobias Poehlmann, Zwickau (DE); Diana Imhof, Jena (DE); Sandra Koehn, Jena (DE)

(73) Assignee: Friedrich-Schiller-Universitaet Jena, Jena (DE)

( * ) Notice: Subject to any disclaimer, the term of this patent is extended or adjusted under 35 U.S.C. 154(b) by 481 days.

This patent is subject to a terminal disclaimer.

(21) Appl. No.: 13/255,033

(22) PCT Filed: Mar. 12, 2010

(86) PCT No.: PCT/DE2010/000284
§ 371 (c)(1),
(2), (4) Date: Sep. 6, 2011

(87) PCT Pub. No.: WO2010/102615
PCT Pub. Date: Sep. 16, 2010

(65) Prior Publication Data
US 2011/0319342 A1   Dec. 29, 2011

Related U.S. Application Data

(63) Continuation of application No. 12/449,419, filed as application No. PCT/DE2008/000279 on Feb. 13, 2008.

(30) Foreign Application Priority Data

Mar. 13, 2009 (DE) .......................... 10 2009 012 871
Sep. 30, 2009 (DE) .......................... 10 2009 043 743

(51) Int. Cl.
*A61K 38/14* (2006.01)
*C12N 15/11* (2006.01)

(52) U.S. Cl.
CPC .......... *C12N 15/111* (2013.01); *C12N 2310/14* (2013.01); *C12N 2310/3513* (2013.01); *C12N 2310/3527* (2013.01); *C12N 2320/32* (2013.01)

(58) Field of Classification Search
CPC ............. C12N 15/111; C12N 2310/14; C12N 210/3527; C12N 2330/32
See application file for complete search history.

(56) References Cited

U.S. PATENT DOCUMENTS

| 5,898,031 | A  | 4/1999 | Crooke |
| 6,107,094 | A  | 8/2000 | Crooke |
| 6,506,559 | B1 | 1/2003 | Fire et al. |
| 7,056,704 | B2 | 6/2006 | Tuschi et al. |
| 7,098,002 | B1 | 8/2006 | Rubinstein et al. |

| 2003/0219375 | A1 | 11/2003 | Piwnica-Worms |
| 2008/0234183 | A1 | 9/2008 | Hallbrink et al. |
| 2010/0009446 | A1 | 1/2010 | Poehlmann et al. |
| 2011/0319342 | A1 | 12/2011 | Poehlmann et al. |

FOREIGN PATENT DOCUMENTS

| WO | WO-2006/019430 | 2/2006 | |
| WO | WO-2007/056153 | 5/2007 | |
| WO | WO 2007/069068 | * 6/2007 | ............. A61K 47/48 |
| WO | WO-2008/098569 | 8/2008 | |

OTHER PUBLICATIONS

May 15, 1991 Netzel-Arnett S et al: "Continousiy recording fluorescent assays optimized for five human matrix metalloproteinases", Analytical Biochemistry, Bd. 195, Nr. 1, May 15, 1991, Seiten 86-92, XP024828075.

Jul. 1, 2001 Turk B E et al: "Determination of protease cleavage site motifs using mixture-based oriented peptide libraries", Nature Biotechnology, Bd. 19, Nr. 7, Jul. 1, 2001, Seiten 661-667, XP002254824.

Apr. 1, 2003 Harborth J et al: "Sequence, chemical, and structural variation of small interfering RNAs and short hairpin RNAs and the effect on mammalian gene silencing", Antisense & Nucleic Acid Drug Development, Bd. 13, Nr. 2, Apr. 1, 2003, Seiten 85-105, XP002284355.

Sep. 1, 2002 Schwarz D S et al: "Evidence That SIRNAS Function as Guides, Not Primers, In the *Drosophila* and Human RNAI Pathways", Molecular Cell, Bd. 10, Nr. 3, Sep. 1, 2002, Seiten 537-548, XP009019083.

Sayda M. Elbashir, et al.; "Duplexes of 21-nucleotide RNAs mediate RNA interference in cultured mammalian cells", Nature, vol. 411 (6836), May 24, 2011, pp. 494-498.

Yinghui Liu, et al.; "Efficient and Isoform-Selective Inhibition of Cellular Gene Expression by Peptide Nucleic Acids", Biochemistry, Feb. 24, 2004, 43 (7), pp. 1921-1927.

Min Zhang, et al.; "Downregulation Enhanced Green Fluorescence Protein Gene Expression by RNA Interference in Mammalian Cells", RNA Biology, May/Jun. 2004, 1(1), pp. 74-77.

(Continued)

*Primary Examiner* — Marcela M Cordero Garcia
(74) *Attorney, Agent, or Firm* — Jordan and Hamburg LLP

(57) ABSTRACT

A biologically inactivated cell-specifically effective molecule for biologically inactive transfection into a target cell to inhibit expression of genes in the target cell after biological activation of the molecule, by bonding to mRNA and with the formation of a RISC complex, the biologically inactivated cell-specifically effective molecule comprising siRNA coupled with at least one peptide via a linker which remains at the siRNA after biological activation of the molecule, the linker comprising an amino Cn linker wherein n is an integer of 1-6. Kits include the molecule or the constituents thereof and transfection reagents in ampoules and injection equipment for injecting mixtures of the ampoule contents into a medium containing a target cell.

14 Claims, 2 Drawing Sheets

(56) References Cited

OTHER PUBLICATIONS

Ian R. Gilmore, et al.; "Delivery strategies for siRNA-mediated gene silencing", Epub, May 22, 2004, Curr Drug Deliv. Apr. 2006, 3 (2), p. 147-5.

Febienne Vernejoul, et al.; "Antitumor Effect of in Vivo Somatostatin Receptor Subtype 2 Gene Transfer in Primary and Metastatic Pancreatic Cancer Models", Cancer Research 62, 2002, pp. 6124-6131.

B Urban-Klein, et al.; "*RNAi-mediated gene-targeting through systemic application of polyethylenimine (PEI)-complexed siRNA in vivo*", Gene Ther, 12 (5), 2005, pp. 461-466.

Yutaka Ikeda, et al.; "Ligand-Targeted Delivery of Therapeutic siRNA", Pharmaceutical Research, vol. 23, No. 8, Aug. 2006, pp. 1631-1640.

Quan N. Nguyen, et al.; "Light controllable siRNAs regulate gene suppression and phenotypes in cells", Biochim Biophys Acta, 1758, (2006), pp. 394-403.

David V. Morrissey, et al.; "Potent and persistent in vivo anti-HBV activity of chemically modified siRNAs", Nature Biotechnology, vol. 23, No. 8, Aug. 2005, pp. 1002-1007.

Makoto Hayakari et al., "A Rapid and Simple Spectrophotometric Assay of Angiotensin-Converting Enzyme", Analytical Biochemistry 84, pp. 361-369 (1978).

S. Shah et al., "Tolerance of RNA interference toward modifications of the 5' antisense phosphate of small interfering RNA", Oligonucleotides 2007 Spring 17(1) pp. 35-43 Abstract.

Jan. 1, 2004 Cancer siRNA therapy by tumor selective delivery with ligand-targeted sterically stabilized nanoparticle, Raymond M. Schiffelers, et al., Nucleic Acids Research, vol. 32, No. 19, pp. 1-10.

Jan. 1, 2006 Antibody-directed cell-type-specific delivery of siRNA, Hans-Peter Vornlocher, Trends in Molecular Medicine, vol. 12, No. 1, pp. 1-3.

Dec. 21, 2004 Tumor imaging by means of proteolytic activation of cell-penetrating peptides, T. Jiang et al., Proceedings of the National Academy of Sciences of USA, vol. 101, No. 51, pp. 17867-17872.

Jan. 1, 2007 Development of a novel systemic gene delivery system for cancer therapy with a tumor-specific cleavable PEG-lipid, H. Hatakeyama et al., Gene Therapy, vol. 14, No. 1, pp. 68-77.

Sep. 1, 2006 Protease-Modulated Cellular Uptake of Quantum Dots, Yan Zhang et al., Nano Letters vol. 6, No. 9, pp. 1-9.

Jun. 1, 2005 "Activity of Stabilized Short Interfering RNA in a Mouse Model of Hepatitis B Virus Replication." D. V. Morrissey et al. Hepatology. pp. 1349-1356.

* cited by examiner

CELL-SPECIFICALLY EFFECTIVE MOLECULES ON THE BASIS OF SIRNA AND APPLICATION KITS FOR THE PRODUCTION THEREOF AND USE THEREOF

CROSS-REFERENCE TO RELATED APPLICATIONS

The present application is the U.S. National Stage of PCT/DE2010/000284, filed Mar. 12, 2010, and is also a continuation-in-part of copending U.S. application Ser. No. 12/449,419, filed Aug. 6, 2009.

BACKGROUND OF THE INVENTION

The invention relates to specific biologically effective molecules on the basis of "short interfering RNA" (siRNA). After their activation said biologically effective molecules interact with the RNA of the target gene and together with special endoribonucleases they form an RNA protein complex known as "RISC" (RNA induced silencing complex). The RISC complex binds to the target mRNA and endonucleases cut the target mRNA. In this way, the gene expression is inhibited and thus the formation of target proteins is prevented.

The biologically effective molecules, which can be cell-specifically activated, can be used, for example, for combating abnormal cells and inhibiting their growth, particularly in the treatment of tumors and virus infections, in senescene-related treatments, etc. Generally, biologically effective molecules, which can be cell-specifically activated, can be used for the modulation of the gene expression of the target cells. But it is not only possible to reduce the expression of genes but also to increase it by achieving a reduction of the expression of the negative regulators of the target gene by means of the biologically active molecules.

The inhibition of the gene expression by introducing short (19-23 bp), double-stranded RNA molecules (siRNA) in eukaryotic cells, which is specific for a sequence segment of the mRNA of a target gene, was already described: Elbashir S M et al.: Duplexes of 21-nucleotide RNAs mediate RNA interference in cultured mammalian cells, Nature, 2001 May 24, 411(6836), 494-8; Liu Y et al.: Efficient and isoform-selective inhibition of cellular gene expression by peptide nucleic acids, Biochemistry, 2004 Feb. 24, 43(7), 1921-7; U.S. Pat. Nos. 5,898,031; 7,056,704).

Such molecules do not serve to inhibit the reading of a gene and the production of an mRNA but the siRNA initiates a cell's own mechanism that decomposes the target mRNA. Finally, the formation of a specific protein is inhibited without impairing the expression of further genes (post-transcriptional gene silencing).

To inhibit the expression of a gene the siRNA molecules can be directly introduced into the cell by transfection reagents and electroporation (Zhang M et al.: Downregulation enhanced green fluorescence protein gene expression by RNA interference in mammalian cells, RNA Biol. 2004 May, 1(1), 74-7; Gilmore IR et al.: Delivery strategies for siRNA-mediated gene silencing, Epub 2004 May 22., Curr Drug Deliv. 2006 Apr., 3(2), 147-5; U.S. Pat. No. 6,506,559).

The disadvantage of this method is the relative instability of the siRNA but it can be improved by chemical modifications (U.S. Pat. No. 6,107,094).

A special problem in the therapeutic application of biologically efficient molecules is an application in vivo. Methods have been introduced for such applications to stabilize the siRNA to reduce the decomposition (Morrissey et. al.: Chemical Modifications of Synthetic siRNA, Pharmaceutical Discovery, May 1, 2005), and transfection reagents, for example nanoparticles, in vivo-jetPEI™ (Polyplus), have been developed that introduce the siRNA into cells in vivo, too (Vemejoul et al.: Antitumor effect of in vivo somatostatin receptor subtype 2 gene transfer in primary and metastatic pancreatic cancer models, Cancer Research 62, 2002, 6124-31; Urban-Klein B, Werth S, Abuharbeid S, Czubayko F, Aigner A: RNAi-mediated gene-targeting through systemic application of polyethylenimine (PEI)-complexed siRNA in vivo, Gene Ther 12(5), 2005, 461-6.).

Furthermore, methods have been developed to increase the transfection of cells of a target gene with siRNA in vivo (Ikeda et. al.: Ligand-Targeted Delivery of Therapeutic siRNA, Pharmaceutical Research, Vol. 23, No. 8, August 2006).

However, the administration of biologically active substances in vivo is often combined with problems due to the systemic effect. The selective introduction of these substances into target cells is not sufficiently specific. This fact is particularly disadvantageous for siRNA molecules that shall have a selective effect only in target cells. Sufficiently high cell specificity is not achieved by tissue- or cell-specifically marked transfection reagents (e.g. antibody/antigen-marked nanoparticles, TAT protein flanking, and others). Though wrong transfections occur in the prior art even when such transfection reagents are used, this does not occur when those transfection reagents are used with the deactivated molecules of the present invention.

A further known method is the deactivation of the biological effect of siRNA molecules by coupling fluorochromes and the re-transfer of said molecules to their active structure by irradiating them with light of a specific wave length (QN Nguyen et al.: Light controllable siRNAs regulate gene suppression and phenotypes in cells, Biochim Biophys Acta, 2006). This activation is initiated from the outside and is, in no way, cell-specifically directed. Consequently, the mentioned siRNA molecules have not only an effect in the corresponding target cells after their activation but, unintentionally, also in all the other transfected cells. Moreover, it is also difficult to apply this mechanism in vivo.

It is also known to deactivate the biological effect of siRNA molecules by coupling peptides that are formed so that these peptides are separated in target cells by target-cell-specific active peptidases whereas they remain inactive in non-target cells (WO002008098569A2). In this way it is possible to very selectively activate molecules on the basis of siRNA in target cells without having a negative effect of said molecules on the cell function in other cells.

Practice has proved that the link of siRNA with the peptides is not without problems and that after the separation of the one peptide or more peptides the linker that remains at the siRNA or also remaining peptide residues impair the efficacy of the siRNA in the target cells. Although the siRNA molecule is effectively deactivated during the peptide coupling, the examined linkers, and possibly also the mentioned peptide residues, that remain at the siRNA after peptide separation have a negative effect on the induction of the RNA interference thus impairing the biological efficacy of the siRNA.

BRIEF SUMMARY OF THE INVENTION

The aim of the invention is to create a link between the siRNA and one peptide or more peptides, wherein the siRNA is activated after peptide separation without the remaining linkers and/or remaining peptide residues significantly impairing the biological efficacy of the siRNA activated in the cell.

According to the invention, a special amino Cn linker (with Cn=C1, C2, C3, C4, C5 or C6), for example an amino C6 linker, is proposed by means of which the siRNA is covalently coupled at its 3' or/and 5' end to the at least one peptide. This covalent coupling deactivates the biologically effective siRNA molecules. Therefore, a specific gene expression is not inhibited after a transfection of such inactive molecules as long as even only one of the coupled peptides remains at the siRNA molecules due to the non-existence of the is corresponding enzyme that is specific for the target cell.

To activate the biologically effective molecules the one peptide or more peptides are separated from the siRNA and the amino Cn linker and possibly a peptide residue remain at the siRNA.

Even if the proposed special linker remains at the siRNA after the separation of the one peptide or more peptides (and possibly peptide residues remain there after separation, too) it was a surprise to see that the remaining linker and possibly the mentioned remaining peptide residues have almost no negative influence (or if any negative influence it is insignificant) on the activated siRNA efficacy of the separated molecule although experts would expect that any part of the molecule that remains at the siRNA reduces the biological efficacy of the siRNA. Linkers, also the amino Cn linker proposed for the siRNA molecule, are known per se but are not used in practice for the coupling of separable peptides. Even experts do not know such applications. In this invention the molecules on the basis of siRNA, which are not broken up by the cell-specific enzymes of the target cell (see WO002008098569A2), remain reliably inactive and are activated with the biological efficacy of the siRNA with the breaking up of the molecules after transfection in or to the target cell.

The inventive effect has been proven by the amino C6 linker but tests have shown that smaller or larger structures of said linker type (such as an amino C2, C3, C4, C5 linker) can be used with a similar effect.

A suitable transfection system including as carriers, for example nanoparticles or envelope molecules, such as liposomes, or lipids or polymers, can be used to transfect the deactivated active ingredient molecules, as known, into the target cells. There, said deactivated covalent bonds can be broken up in a cell-specific manner by the one or more cell-specific enzyme's that is/are relevant for the bonding to sequences of the one or more coupling peptide/s, and thus the biological efficacy of the molecule that is now in the target cell and separated from peptides is activated. Then, said molecule couples to the specific mRNA of the target cell and thus it inhibits, also in a known manner, the gene expression in this specific cell.

In all the other cells of the organism different from the predefined target cells in which said molecule constructs can also enter, the active ingredient molecules remain reliably inactive because the covalent bonds between the biologically effective molecule, particularly siRNA, and the one peptide or more peptides are kept completely (no peptide bonds have been broken up) or partly (not all peptide bonds have been broken up) due to the non-existence of the one or more target-cell-specific enzyme/s. The biologically effective molecule does not link with the mRNA of this cell, or RISC is not initiated, due to the still covalent peptide bond.

Although, for example, in tumor therapy the inventive molecule constructs, which are to be transfected, do not only enter into or to tumor-diseased target cells in their inactive (coupled) form but (as it can almost not be avoided in practical treatments) can also reach healthy cells, the biological efficacy of said molecule is only selectively activated in or at the tumor-diseased target cells by the cell-specific enzymes existing there and the expression of the target gene influenced by the active ingredient is effectively inhibited. This gene expression and thus the protein formation for the further existence of the healthy cells remain unaffected by this active ingredient although the molecule constructs are in these not diseased cells (or for the intended biological effect not desired cells) because they are permanently inactive here.

Thanks to the proposed highly selective efficacy of the molecules that is achieved by the target cell enzyme-specific inactivity/activation, the biologically inactive molecule constructs with the appropriate peptide coupling that are to be transfected can be administered systemically.

The molecule constructs can be linked to further substances (e.g. nanoparticles as carrier system) to guarantee their better transport and stabilization.

In this invention these wrong transfections cannot be avoided but the wrongly transfected molecules, even if they are still not desired, are biologically inactive in the cells that are not the target cells. This status does not change even despite the molecule activation in or at the target cells so that the biological efficacy is selectively developed only in the target cells and, contrary to known mechanisms, the highly cell-selective modulation of the gene expression is achieved.

Moreover, it can be taken into consideration to use also smaller double-stranded RNA molecules instead of 18-23 bp siRNA molecules.

The application possibilities of such molecules with a covalent bond of the siRNA to one peptide or more peptides are already mentioned in the WO002008098569A2.

According to a further aspect of the invention, it is advantageous to use an application kit in which the biologically effective molecules that are to be introduced and coupled via a selectable linker with the selectable peptides (see WO002008098569A2) are provided. Said application kit in form of an ampoule should contain all required ingredients, practicably also a selection of suitable transfection systems (such as nanoparticles, synthetic polymers such as polyethylene, or lipids as carriers), other transfection reagents (such as antibodies, ligands, antigen markers, other tissue- or cell-specifically marked transfection reagents referred to hereinabove in connection with the background of the invention, and polyethylene glycol) as well as one probe or more probes or syringes with canula for injecting the mixture from the ampoule contents into the medium that contains the target cells. According to an added instruction for applying and administering the molecules, the user can produce appropriate application mixtures for the intended use and apply them. Furthermore, an alternative application kit would enable producing said inactivated biologically effective molecule.

One exemplary application kit according to the invention includes:

a first ampoule containing the biologically inactivated cell-specifically effective molecule, the molecule being cell-specifically effective for the target cell;

a second ampoule containing transfection reagents;

dilution and reaction buffers for the contents of the first and second ampoules; and at least one probe or syringe having canula for injecting mixtures of the contents of the ampoules into a medium that contains the target cells.

Another exemplary application kit according to the invention includes:

a first ampoule containing a linker and at least one peptide for coupling with siRNA through the linker to deactivate the siRNA, the linker comprising an amino Cn wherein n is an integer of 1-6;
a second ampoule containing the siRNA and reaction buffers for coupling the at least one peptide to the siRNA;
a third ampoule for modifying the at least one peptide after coupling of the at least one peptide to the siRNA;
a fourth ampoule containing further reaction buffers;
a system for purifying subproducts or final products after the coupling of the at least one peptide to the siRNA; and
at least one probe or syringe having canula, for injecting a mixture of contents of the ampoules into a medium containing the target cell.

The application kits may also include other equipment, such as dialysis membranes and reaction vessels.

Of course, the kits would typically include instructions for their use.

It is an appropriate measure to provide such application kits specifically is for the selected target cells and target genes and for the individual range of application (in vitro or in vivo).

BRIEF DESCRIPTION OF THE DRAWINGS

The invention will be explained in more detail by virtue of the embodiment with the amino C6 linker as shown in the drawings.

They show.

DETAILED DESCRIPTION OF THE INVENTION

Figure 1:
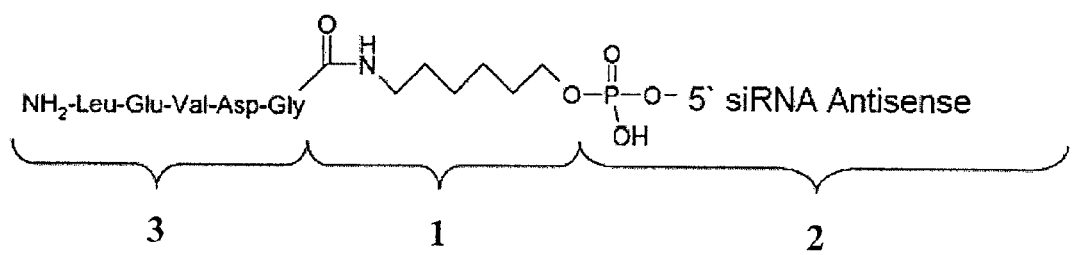
FIG. 1: deactivated siRNA molecule by means of coupling the siRNA via the amino C6 linker with the peptide; chemical structure of the amino C6 linker

FIG. 1 shows as an example of an amino Cn linker with Cn=C1, C2, C3, C4, C5 or C6 the chemical structure of an amino C6 linker known per se. Via this amino C6 linker 1 an siRNA 2 is coupled with a peptide 3 for its biological deactivation (deactivation of the effect of the siRNA in a cell). The amino C6 linker 1 is coupled with the siRNA 2 via the 5' end of the antisense strand of said siRNA. As long as the peptide is coupled to this siRNA molecule the siRNA molecule remains biologically deactivated.

Figure 2:
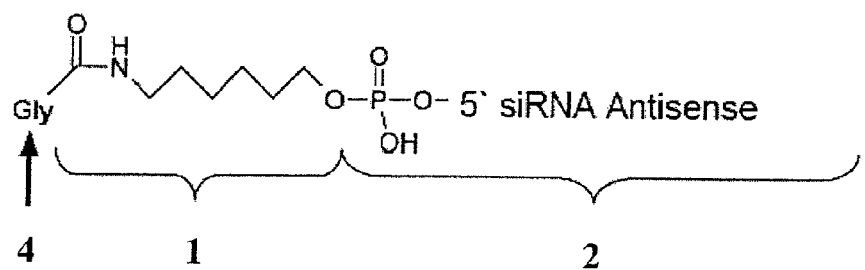
FIG. 2: cell-specifically activated siRNA molecule in which the peptide bond is broken up and the amino C6 linker as well as a peptide residue remain at the siRNA molecule

If the peptide bond is broken up by a cell-specific enzyme of a target cell into which the deactivated siRNA molecule was transfected as shown in FIG. 2 (complete separation of all peptides 3), the remaining siRNA molecule will be biologically activated by activating the known cell-specific effect of the siRNA intended by the molecule transfection (see is also WO002008098569A2).

Surprisingly, this activation takes place although the amino C6 linker 1 and possibly a residue of the peptide 3 remain at the residue of the siRNA molecule after the mentioned breaking up of the peptide bond (see FIG. 2), i.e. said biological effect of the siRNA 2 is not impaired or insignificantly impaired by the amino C6 linker 1 and the residues of the peptide 4 remaining at the molecule.

Figure 3:
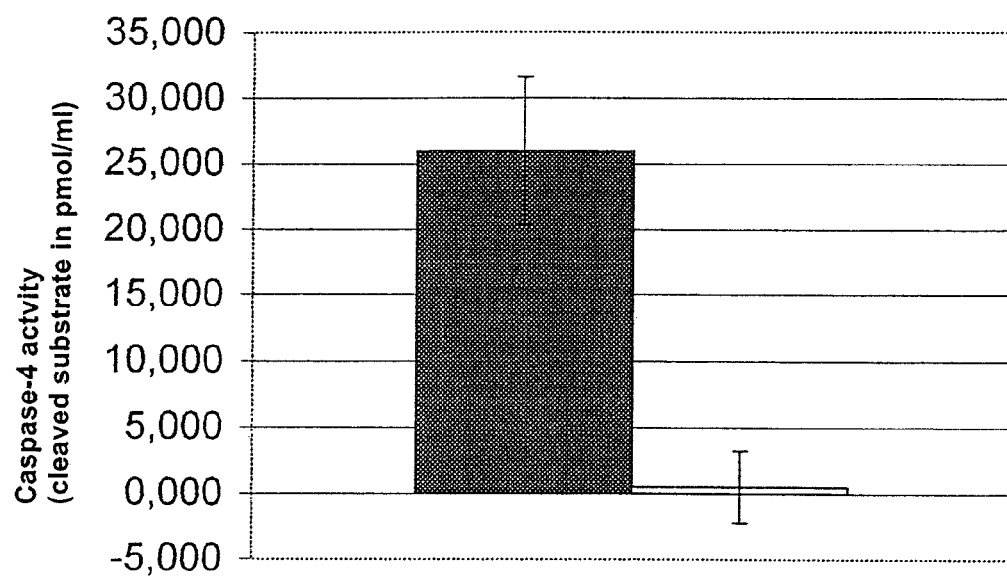
FIG. 3: enzyme activity of caspase-4 in target and non-target cells

FIG. 3 shows the cell-specific activity of the cleavage enzyme caspase-4. Here, the enzyme caspase-4 is active in the target cells (Jeg-3 choriocarcinoma cells; dark diagram bar) but not active in the non-target cells (human embryonic kidney, HEK; bright diagram bar). As a result, a siRNA, which has been inhibited by coupling the target peptide for caspase-4 via the linker structure of FIG. 1, is separated in the caspase-4-containing target cells and activated in this way.

Figure 4:
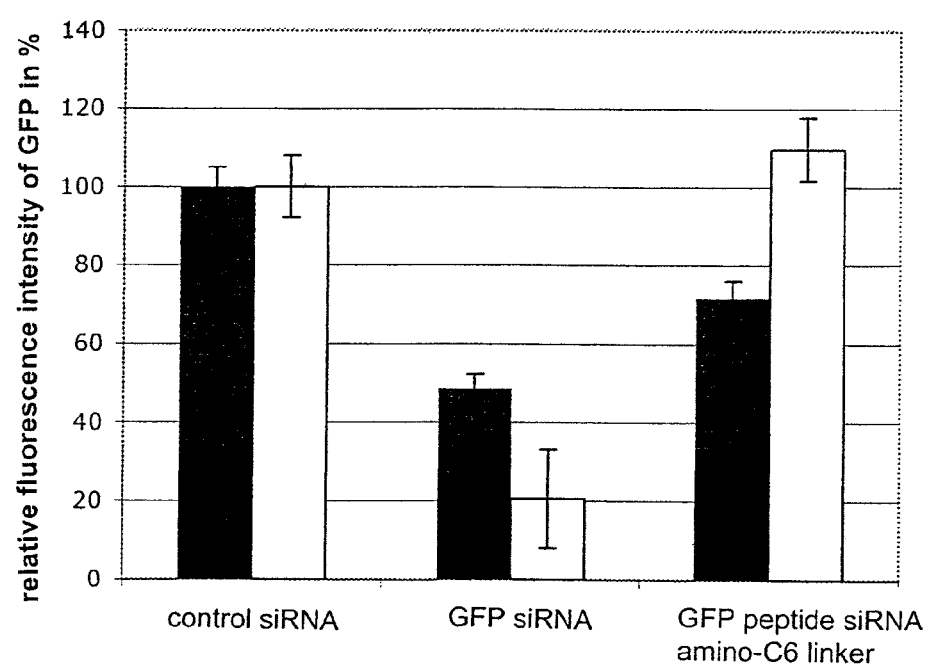
FIG. 4: representation of the cell specific reduction of the expression of the GFP gene by peptide-inhibited siRNA

FIG. 4 represents the detection fluorescence intensities when introducing a control siRNA without function, a siRNA for the reduction of the expression of the GFP gene and a peptide-inhibited siRNA that can be activated by caspase-4. The reduction of the fluorescence correlates with the biological activity of the siRNA. It can be observed that the siRNA is activated in the target cells (Jeg-3 choriocarcinoma cells; dark diagram bar) and thus the expression of the GFP gene is reduced, whereas in the non-target cells the expression of this gene is not reduced (human embryonic kidney, HEK; bright diagram bar). Even if the linker structure and a peptide residue (in this case an amino C6 linker with bonded glycine) remain at the activated siRNA, the effect of the siRNA can be compared with the effect of normal siRNA.

The invention claimed is:

1. A biologically inactivated molecule for biologically inactive transfection into a target cell that becomes specifically effective in the target cell upon biological activation therein in order to inhibit expression of genes in the target cell by bonding to mRNA to form a RISC complex, the biologically inactivated molecule comprising a linker consisting of an amino-$C_n$ linker directly coupled at a first linker end to at least one peptide and directly coupled at a second linker end to siRNA, n being an integer of 1-6.

2. The biologically inactivated molecule according to claim 1, wherein n is 6.

3. The biologically inactivated molecule according to claim 1, wherein n is 5.

4. The biologically inactivated molecule according to claim 1, wherein n is 4.

5. The biologically inactivated molecule according to claim 1, wherein n is 3.

6. The biologically inactivated molecule according to claim 1, wherein n is 2.

7. The biologically inactivated molecule according to claim 1, wherein n is 1.

8. A composition comprising biologically inactivated molecules according to claim 1, a carrier comprising transfection reagents selected from the group consisting of nanoparticles marked with a ligand, antibody or antigen for cell-specific transfection, and nanoparticles, polymers and lipids for enveloping the biologically inactivated molecules for their transfection, or reagents for transfection by lipid-based methods or TAT protein flanking.

9. A kit for transfection of a biologically inactivated molecule which is specifically effective for a target cell, the kit comprising
a first ampoule containing the biologically inactivated molecule of claim 1;
a second ampoule containing transfection reagents;
dilution and reaction buffers for the contents of the first and second ampoules; and
at least one probe or syringe having a cannula for injecting mixtures of the contents of the ampoules into a medium that contains the target cells.

10. The kit according to claim 9 wherein the transfection reagents are selected from the group consisting of nanoparticles marked with a ligand, antibody or antigen for cell-specific transfection, and nanoparticles, polymers and lipids for enveloping the biologically inactivated molecules for their transfection, or reagents for transfection by lipid-based methods or TAT protein flanking.

11. A kit for transfection of a biologically inactivated molecule which is specifically effective for a target cell, the kit comprising a first ampoule containing a linker and at least one peptide for directly coupling with siRNA though the linker to deactivate the siRNA, the linker consisting of an amino $C_n$, linker wherein n is an integer of 1-6;

a second ampoule containing the siRNA and reaction buffers for directly coupling the at least one peptide to the siRNA;

a third ampoule for modifying the at least one peptide after the direct coupling of the at least one peptide to the siRNA;

a fourth ampoule containing further reaction buffers;

a system for purifying sub-products or final products after the coupling of the at least one peptide to the siRNA; and at least one probe or syringe having a cannula for injecting a mixture of contents of the ampules into a medium containing the target cell.

12. The kit according to claim 11, further comprising equipment selected from the group consisting of dialysis membranes and reaction vessels.

13. A biologically inactivated molecule of the following formula: t,?

the molecule being effective for biologically inactive transfection into a target cell and for becoming biological active in the target cell, the molecule, upon biological activation, inhibiting the expression of genes in the target cell by bonding to mRNA and forming a RISC complex, wherein, in the above formula, 1 is a linker, 2 is siRNA, 3 is a peptide, A is $C_n$, and n is an integer of 1-6.

14. The biologically inactivated molecule according to claim 13, wherein n is 6.

* * * * *